US009137462B2

(12) United States Patent
Li et al.

(10) Patent No.: US 9,137,462 B2
(45) Date of Patent: Sep. 15, 2015

(54) HOUGH TRANSFORM APPROACH TO GAP MEASUREMENT IN BLADE INSPECTION

(75) Inventors: Gang Li, Princeton, NJ (US); Yakup Genc, Dayton, NJ (US); Erwan Baleine, Orlando, FL (US); Dennis H. Lemieux, Casselberry, FL (US)

(73) Assignees: Siemens Corporation, Iselin, NJ (US); Siemens Energy, Inc., Orlando, FL (US)

( * ) Notice: Subject to any disclaimer, the term of this patent is extended or adjusted under 35 U.S.C. 154(b) by 363 days.

(21) Appl. No.: 13/617,416

(22) Filed: Sep. 14, 2012

(65) Prior Publication Data

US 2013/0088587 A1    Apr. 11, 2013

Related U.S. Application Data

(60) Provisional application No. 61/537,712, filed on Sep. 22, 2011.

(51) Int. Cl.
*G01N 29/27* (2006.01)
*H04N 5/33* (2006.01)
(Continued)

(52) U.S. Cl.
CPC .. *H04N 5/33* (2013.01); *G06T 7/60* (2013.01); *G06T 7/602* (2013.01); *G01N 2223/63* (2013.01); *G06T 7/0004* (2013.01); *G06T 2207/10048* (2013.01); *G06T 2207/20061* (2013.01); *G06T 2207/20096* (2013.01); *G06T 2207/20101* (2013.01); *G06T 2207/30164* (2013.01)

(58) Field of Classification Search
CPC .......... G01S 13/88; G01B 7/14; G01R 27/26; G01R 27/04

USPC .................. 348/94, 92, 86, 82, 61; 702/151; 33/656; 324/230, 207
See application file for complete search history.

(56) References Cited

U.S. PATENT DOCUMENTS 4,346,383 A * 8/1982 Woolcock et al. ............ 342/127
5,445,027 A    8/1995 Zorner
(Continued)

FOREIGN PATENT DOCUMENTS

JP    2011059742 A    3/2011

OTHER PUBLICATIONS

Claudio Rosito Jung and Rodrigo Schramm, "Rectangle Detection based on aWindowed Hough Transform", UNISINOS— Universidade do Vale do Rio dos Sinos Ciencias Exatas e Tecnologicas; 2004; Av. UNISINOS, 950. S~ao Leopoldo, RS, Brasil, 93022-000, p. 1-8.*
(Continued)

*Primary Examiner* — Sath V Perungavoor
*Assistant Examiner* — Clifford Hilaire

(57) ABSTRACT

Two adjacent objects with a gap between the objects rotate in a hot atmosphere with a temperature greater than 300 F in a gas turbine. Automatic and accurate contactless measurement of the gap is performed by taking images of the gap. An image, preferably an infra-red image is taken from the gap, a processor extracts the two edges from the image of the gap. The processor also determines a line through the pixels of an edge by applying a Hough transform on the pixels. The edges are substantially parallel. A line substantially perpendicular to the lines is also determined. Using the substantially parallel lines and the line substantially perpendicular to the substantially parallel lines the processor determines a width of the gap.

20 Claims, 5 Drawing Sheets

(51) Int. Cl.
*G06T 7/60* (2006.01)
*G06T 7/00* (2006.01)

(56) References Cited

U.S. PATENT DOCUMENTS

| | | | |
|---|---|---|---|
| 5,796,856 A * | 8/1998 | Graff et al. | 382/108 |
| 6,992,315 B2 | 1/2006 | Twerdochlib | |
| 7,064,811 B2 | 6/2006 | Twerdochlib | |
| 7,432,505 B2 | 10/2008 | Brummel | |
| 7,489,811 B2 | 2/2009 | Brummel | |
| 2005/0264275 A1 * | 12/2005 | Bosselmann et al. | 324/71.1 |
| 2008/0149049 A1 * | 6/2008 | Mollmann et al. | 123/2 |
| 2012/0044343 A1 | 2/2012 | Kurihara | |

OTHER PUBLICATIONS

Jung, Claudio Rosito, and Rodrigo Schramm. "Rectangle detection based on a windowed Hough transform." Computer Graphics and Image Processing, 2004. Proceedings. 17th Brazilian Symposium on. IEEE, 2004.*

R. Duda, P. Hart, Use of the Hough Transform to detect lines and curves in pictures. Technical Note 36, Apr. 1971, Stanford Research Institute, Menlo Park, CA, 18 pages.

PCT International Search Report mailed Jan. 7, 2014 corresponding to PCT International Application No. PCT/US2013/059587 filed Sep. 13, 2013 (14 pages).

Brummel, Hans-Gerd, et al.; "Online Monitoring of Gas Turbine Power Plants;" XP055093547; retrieved from the Internet: URL: http://www.energy.siemens.com/mx/pool/hq/energy-topics/pdfs/en/gas-turbines-power-plans/4_Online_Monitoring_of_Gas.pdf; Section 6, Figs. 11-17; 2005; Jan. 1, 2005.

Lambert, P., et al; "Thickness Measurement of Food Packing Films," Int'l. Conference on Quality Control by Artificialvision—Conference Int'l. Sur Le Controle Qualitepar Vision Artificielle, XX, XX; XP009053845; 1999; May 18, 1999.

Sun, Yan, et al.; "Research on Detection Method of End Gap of Piston Rings Based on Area Array CCD and Image Processing;" 2012 Int'l. Workshop on Image Processing and Optical Engineering, SPIE, 1000 20th St., Bellingham, WA 98225-6705; vol. 4335, No. 1; XP060000560; 2012; US; Jan. 24, 2012.

* cited by examiner

HOUGH TRANSFORM APPROACH TO GAP MEASUREMENT IN BLADE INSPECTION

CROSS-REFERENCE TO RELATED APPLICATION

This application claims the benefit of U.S. Provisional Application No. 61/537,712, filed Sep. 22, 2011 the disclosure of which is incorporated by reference herein in its entirety.

TECHNICAL FIELD

The present invention relates to image based non-contact measurement of a gap between blades in a turbine in operation at temperatures of 300 F and higher.

BACKGROUND

A camera may be used to measure a gap between different blades of a machine such as a gas turbine. When the machine is in operation, gaps between adjacent blades may change their widths during different phases of operation, for instance as a result of changed temperature, changed pressure or operational stresses. Detecting and accurately measuring these gaps can provide relevant information about operating conditions and machine performance. Measuring a gap accurately and automatically is challenging even with known main axis of orientation of the parts. For instance, an infra-red camera is used to measure a gap in a hot environment of a turbine. Accurately detecting and measuring the gap with an infra-red camera is challenging because the infra-red images have low contrast, and the signal to noise ratio (SNR) is low. Furthermore, it is preferred to monitor such a gap over a significant period of time of uninterrupted operation. Simple and effective methods and apparatus to automatically measure gaps in an uninterrupted in hot operating environments are believed currently not to exist.

Accordingly, novel and improved apparatus and methods are required to accurately and automatically measure and monitor in a non-contact manner a gap between parts in a machine in a hot operating environment are required.

SUMMARY

Methods to automatically measure a width of a gap between moving parts in a machine from images of the gap are provided.

In accordance with an aspect of the present invention a method is provided to measure a width of a gap between two moving parts in a machine, comprising: recording an image of the gap with an infra-red camera and storing the image as image data, a processor extracting a first and a second edge related to the gap from the image data, the processor applying a Hough transform to a plurality of pixels of the first edge to determine a first line and to a plurality of pixels of the second edge to determine a second line, substantially parallel to the first line, applying a line that crosses the first and second lines and the processor determining the width of the gap by applying the first and second line and the line that crosses the first and second lines.

In accordance with an aspect of the present invention a method is provided, wherein the Hough transform applies voting related to the plurality of pixels of the first edge to eliminate line parameters caused by noise in the image data.

In accordance with an aspect of the present invention a method is provided, wherein a position of the line that crosses the first and second lines is determined by a user.

In accordance with an aspect of the present invention a method is provided, wherein the machine is a turbine with moving turbine blades.

In accordance with an aspect of the present invention a method is provided, wherein the gap is between two adjacent blades of a turbine.

In accordance with an aspect of the present invention a method is provided, wherein the width of the gap is determined a plurality of times over a period of at least 6 hours.

In accordance with an aspect of the present invention a method is provided, wherein the width of the gap is measured with an accuracy of at least 0.1 mm.

In accordance with an aspect of the present invention a method is provided, wherein the first and second edges related to the gap are extracted from the image data by a Canny edge detector.

In accordance with an aspect of the present invention a method is provided, wherein the moving parts are rotating parts with a rotational speed of more than 300 revolutions per minute.

In accordance with an aspect of the present invention a method is provided, wherein the two adjacent blades are rotating with a rotational speed of at least 300 revolutions per minute in an atmosphere with a temperature of at least 300° F.

In accordance with a further aspect of the present invention a system is provided to measure a width of a gap between two moving parts in a machine, comprising: an infra-red camera to record an image of the gap, a memory to store the image of the gap as image data, a processor to execute instructions to perform the steps: extracting a first and a second edge related to the gap from the image data, applying a Hough transform to a plurality of pixels of the first edge to determine a first line and to a plurality of pixels of the second edge to determine a second line, applying a line that crosses the first and second lines and determining the width of the gap by applying the first and second line and the line that crosses the first and second lines.

In accordance with yet a further aspect of the present invention a system is provided, wherein the Hough transform applies voting related to the plurality of pixels of the first edge to eliminate line parameters caused by noise in the image data.

In accordance with yet a further aspect of the present invention a system is provided, wherein a position of the line that crosses the first and second lines is determined by a user.

In accordance with yet a further aspect of the present invention a system is provided, wherein the machine is a turbine with moving turbine blades.

In accordance with yet a further aspect of the present invention a system is provided, wherein the gap is between two adjacent blades of a turbine.

In accordance with yet a further aspect of the present invention a system is provided, wherein the width of the gap is determined a plurality of times over a period of at least 6 hours.

In accordance with yet a further aspect of the present invention a system is provided, wherein the width of the gap is measured with an accuracy of at least 0.1 mm.

In accordance with yet a further aspect of the present invention a system is provided, wherein the first and second edges related to the gap are extracted from the image data by a Canny edge detector.

In accordance with yet a further aspect of the present invention a system is provided, wherein the moving parts are rotating parts with a rotational speed of more than 300 revolutions per minute.

In accordance with yet a further aspect of the present invention a system is provided, wherein the two adjacent blades are rotating with a rotational speed of at least 300 revolutions per minute in an atmosphere with a temperature of at least 300° F. In accordance with an aspect of the present In accordance with another aspect of the present invention, a system to perform the steps described herein is also provided. The system includes a memory enabled to store data including instructions and a processor enabled to execute instructions to perform the steps described herein.

DRAWINGS

FIG. 1 provides different quality images by an infra-red camera of two moving machine parts and the gap between them in accordance with an aspect of the present invention.

DESCRIPTION

In accordance with an aspect of the present invention a width of a gap between two parts in a hot operating environment (at least higher than 300 F) is measured and monitored with an infra-red camera. The two parts in one embodiment of the present invention are turbine blades in a gas turbine and the gap is measured during operation of the turbine. An image of the gap is captured with an infra-red camera and the image is stored by the processor as image data which is further processed by the processor in accordance with various aspects of the present invention. It is already known that the width of a gap between two blades in a gas turbine during operation will change measurably. However, accurately detecting and measuring such a gap width is challenging because infra-red images have low contrast and the signal-to-noise ratio (SNR) is low.

Installing and applying an infra-red camera in a hot part of a gas turbine for inspection has been described in U.S. Patent Application Publication Ser. No. 20060088793, to Brummel, published on Apr. 27, 2006.

Figure 1:
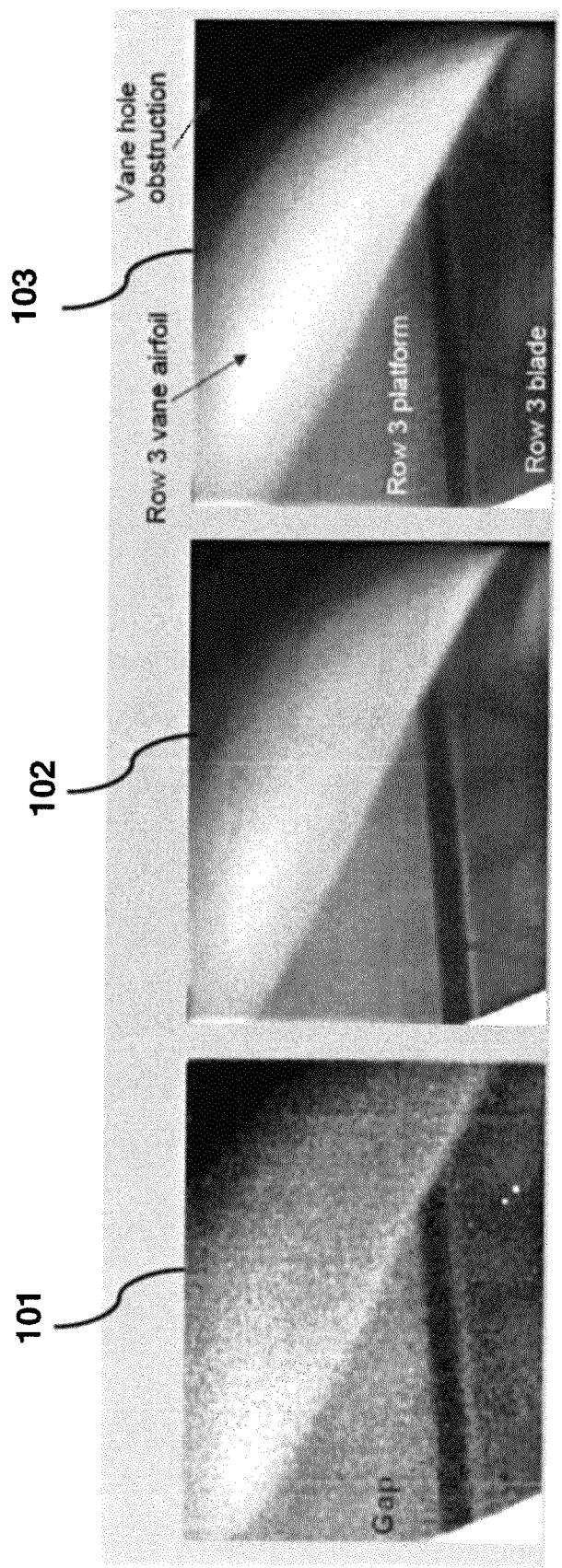

FIG. 1 illustrates examples of IR and IR related images of turbine blades. FIG. 1 contains images 101, 102 and 103 taken with an infra-red camera at three different times. One can observe that: (1) image 101 has a low SNR; (2) the gap varies in size over time; (3) the gap appears on different places in the image, depending when on when the image was taken.

A challenge that has to be addressed is extracting and finding and identifying the gap in an IR image in a manner that allows the gap to be measured from the extracted gap features in a consistent and automatic manner.

A Hough Transform Approach to Gap Measurement

Because the SNR in some images is low, measuring the gap can be challenging. In accordance with an aspect of the present invention the Hough transform is used for gap measurement. The Hough transform is a feature extraction technique to find imperfect instances of objects within a certain class of shapes by a voting procedure. The voting procedure is usually performed in the parameter space of the shape under investigation.

Figure 2:
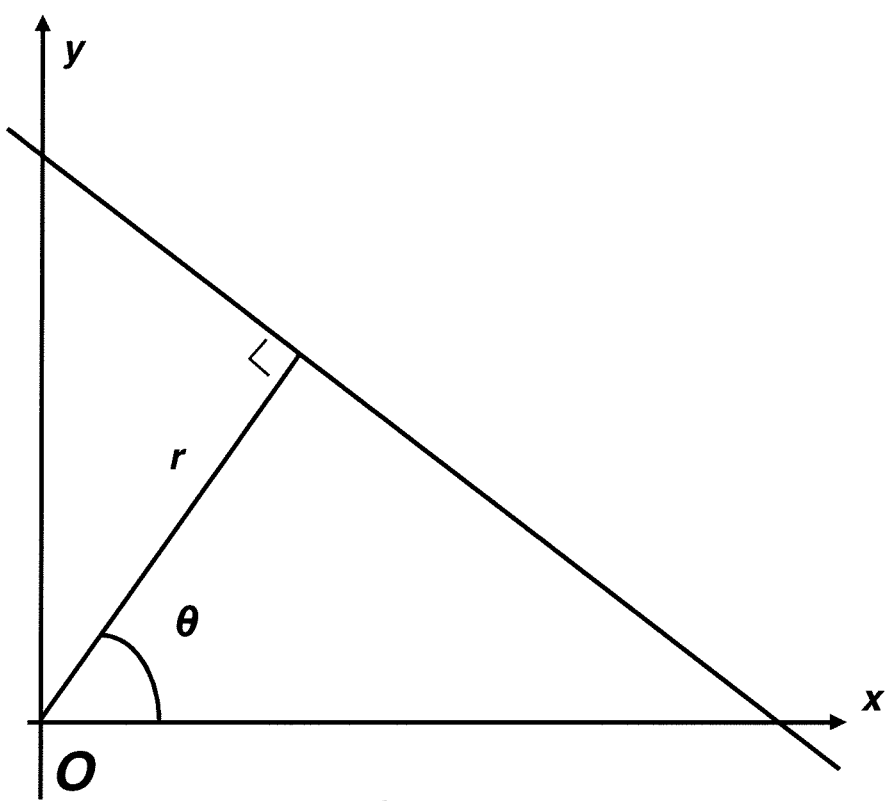
FIGS. 2-4 illustrate the Hough transform.

In accordance with an aspect of the present invention the Hough transform is used as the linear transform for detecting straight lines, as the edges of the blades that form the gaps are straight edges. In the image space, the straight line can be described as y=mx+b and can be graphically plotted for each pair of image points (x, y). In the Hough transform, a main idea is to consider the characteristics of the straight line not as image points $(x_1, y_1)$, $(x_2, y_2)$, etc., but instead, in terms of its parameters, i.e., the slope parameter in and the intercept parameter b. Based on that fact, the straight line y=mx+b can be represented as a point (b, m) in the parameter space. However, one faces the problem that vertical lines give rise to unbounded values of the parameters m and b. For computational reasons, it is therefore better to use a different pair of parameters, denoted r and θ (theta), for the lines in the Hough transform. This is illustrated in FIG. 2 for a line through (0,y) and (x,0).

The parameter r represents the distance between the line and the origin while θ is the angle of the vector from the origin to this closest point. Using this parameterization, the equation of the line can be written as:

$$y = \left(-\frac{\cos\theta}{\sin\theta}\right)x + \left(\frac{r}{\sin\theta}\right)$$

which can be rearranged to r=x cos θ+y sin θ.

It is therefore possible to associate with each line of the image a pair (r,θ) which is unique if θ∈[0,π) and r∈□, or if θ∈[0, π) and r≥0. The (r,θ) plane is sometimes referred to as Hough space for the set of straight lines in two dimensions. This representation makes the Hough transform conceptually very close to the two-dimensional Radon transform.

For an arbitrary point on the image plane with coordinates, e.g., $(x_0, y_0)$, the lines that go through it are determined by $r(\theta)=x_0 \cdot \cos\theta+y_0 \cdot \sin\theta$, where r (the distance between the line and the origin) is determined by θ.

This corresponds to a sinusoidal curve in the (r,θ) plane, which is unique to that point. If the curves corresponding to two points are superimposed, the location (in the Hough space) where they cross corresponds to a line (in the original image space) that passes through both points. More generally, a set of points that form a straight line will produce sinusoids which cross at the parameters for that line.

One aspect of the application of the Hough transform on a set of pixels in the image is the construction of all possible lines through the elements (or pixels), wherein a line is determined by its (r,θ) parameters. Each element or pixel supports a number of lines through it, each with different (r,θ) parameters. One may say that each image point "votes" for all lines (or set of (r,θ) parameters related to a line) going through it. One may create bins, each bin being associated with a set of (r,θ) parameters and containing the number of points or pixels in the image (for instance on an extracted edge) that have the line associated with a specific (r,θ) parameter through it. Each bin accumulates votes (or number of points/pixels that supports the specific line). The bin with the highest number of votes is determined to be the "winner" and to represent the line that goes through most of the points. The concept of "voting" is an application of the histogram of (r,θ) parameters as disclosed in "Richard Duda and Peter Hart, Use of the Hough Transformation to Detect Lines and Curves in Pictures, Technical Note 36, April 1971, Stanford Research Institute, Menlo Park, Calif., Artificial Intelligence Center, published in the Comm. ACM, Vol 15, No. 1, pp. 11-15, January 1972, New York, N.Y."

Figure 3:
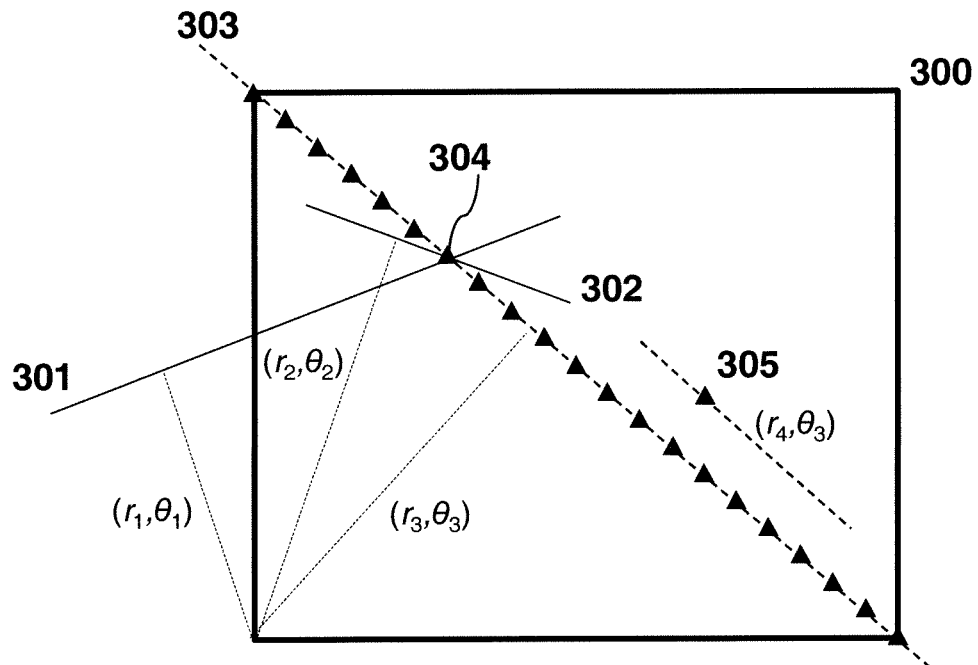

The process of determining the set of (r,θ) parameters from image pixels is further illustrated in FIG. 3 in an image 300 with a set of pixels illustrated by solid triangles. Through each triangle or pixel all possible lines determined by their (r,θ) parameters are constructed.

This is illustrated for one pixel 304, through which lines 301 (with parameters $(r_1,\theta_1)$), line 302 (with parameters $(r_2,\theta_2)$) and line 303 (with parameters $(r_3,\theta_3)$). One can easily see that the line 303 is the only straight line that includes all the pixels except for pixel 305. Pixel 305 is an outlier with parameters $(r_4,\theta_3)$). By creating a histogram or bins related to each set of parameters (r,θ), or collect votes related to each parameter set, one would find that $(r_3,\theta_3)$ has collected most votes and line 303 would be selected as the line with most votes.

Figure 4:
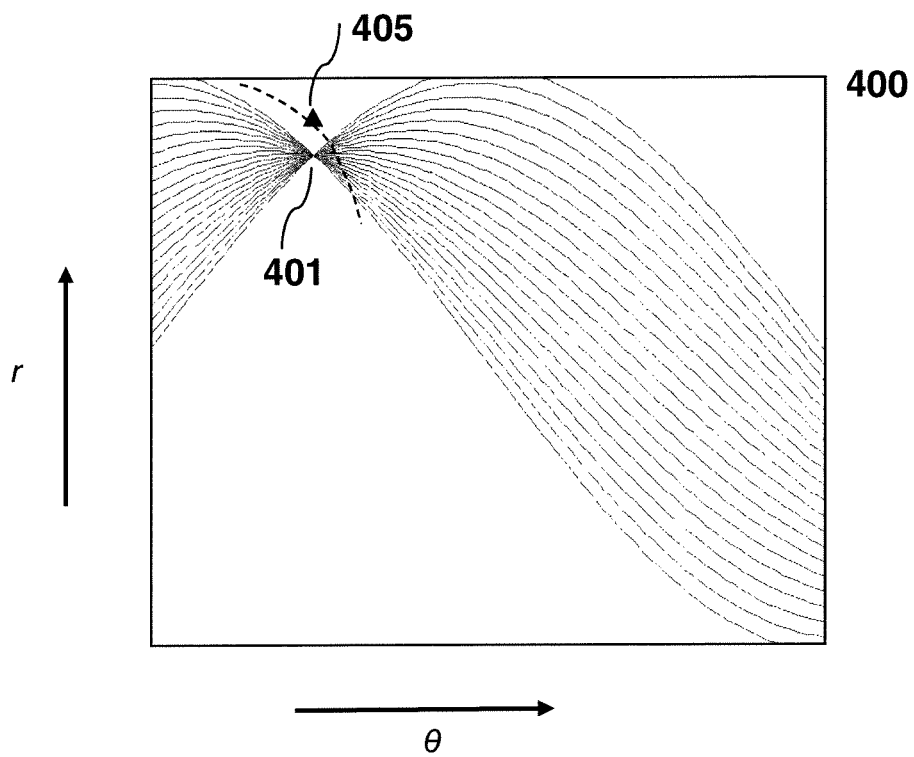

One can create a plot of all parameter sets in plot 400 shown in FIG. 4, which illustrate the sinusoidal curves associated with each point, element or pixel. The sinusoidal curves of the pixels on line 303 have point 401 in common. Point or pixel 305, which is not on 303 has a line parallel to 303 with parameters $(r_4,\theta_3)$ and $r_4>r_3$. Part of the sinusoidal curve through 405 is illustrated in an non-exact way for illustrative purposes in FIG. 4 to show that this curve will not have point 401 in common with the other curves associated with pixels on the line 303. Point 305 thus will not be in the bin of parameters $(r_3,\theta_3)$ and will only have a minority vote. The majority vote will determine the line by using the Hough transform.

In accordance with an aspect of the present invention an automatic gap measurement system based on Hough transform is implemented. For each new image and in accordance with an aspect of the present invention edge detection is applied. In one embodiment of the present invention a Canny edge detection method is applied.

A processor detects and extracts from image data a first edge representing one side of the gap and a second edge representing the other side of the edge.

In a next step a Hough transform is applied on the edge images or the pixels of the edges to detect the two substantially parallel lines that define the gap. The distance between two boundary lines is then computed along a perpendicular direction. Such a line in one embodiment of the present invention is predefined by a user, for instance before the sequence starts. In one assumption the gap over time does not fundamentally change its orientation in the field of view.

In accordance with an aspect of the present invention a voting procedure in the Hough transform method over the set of parameterized image objects is applied to pixels on the extracted edges. These edges being from noisy IR images may have some outliers. The Hough voting procedure is applied to discard the outliers caused by noise and a clean line can be determined from applying the Hough transform to the extracted edges from the infra-red image.

In one embodiment of the present invention the two edges are substantially parallel. Though noise and other effects can influence the extracted edges and the calculated lines through the pixels of an edge, the edges may be assumed to be substantially parallel. In one embodiment of the present invention the two edges are parallel with an angle of 5 degrees or less, preferably within an angle of 2 degrees or less and most preferably within an angle of 1 degree or less. Images demonstrate that such assumptions of the edges being substantially parallel are not unreasonable. This means that one can define a distance of a gap by constructing a line that is substantially perpendicular to the edges or there related lines with at least 5 degrees, preferably within at least 1 degree and most preferably within an angle of 1 degree.

A user may define the line along which the distance is measured between the two extracted lines that define the gap. That line may be generated by the processor as being perpendicular to at least one line determined by the Hough transform. A user may also define a location or a region in the image where the gap is being measured, as the gap may appear at different places on an image based on a trigger for the camera. For instance, one may generate a first image of the gap, detect and extract the edges. If several edges appear, a user in one embodiment identifies a region in the images where a processor should detect the edges of the gap and process the edges or the pixels of the edges with the Hough transform to define the lines of the gap. One may also provide a general direction of a line which should be considered, so that other edges are ignored. The processor generates the two lines that define the gap. A user confirms that two generated lines represent the gap. A user may identify at least one point through which a line perpendicular to the gap should be drawn by the processor.

The processor, based on the calculated gap lines, then generates a line substantially perpendicular to the gap edges. The processor may draw the detected gap edges, the calculated gap lines and the line perpendicular to the edge on the display. Based on the perpendicular line and the gap lines the processor then calculates the distance between the gap lines. If the gap lines are not parallel, for instance due to reflection, noise or other effects, a line may be drawn perpendicular to one of the lines determined by the Hough transform and the point where this perpendicular line crosses the other line is used to determine the distance.

Figure 5:
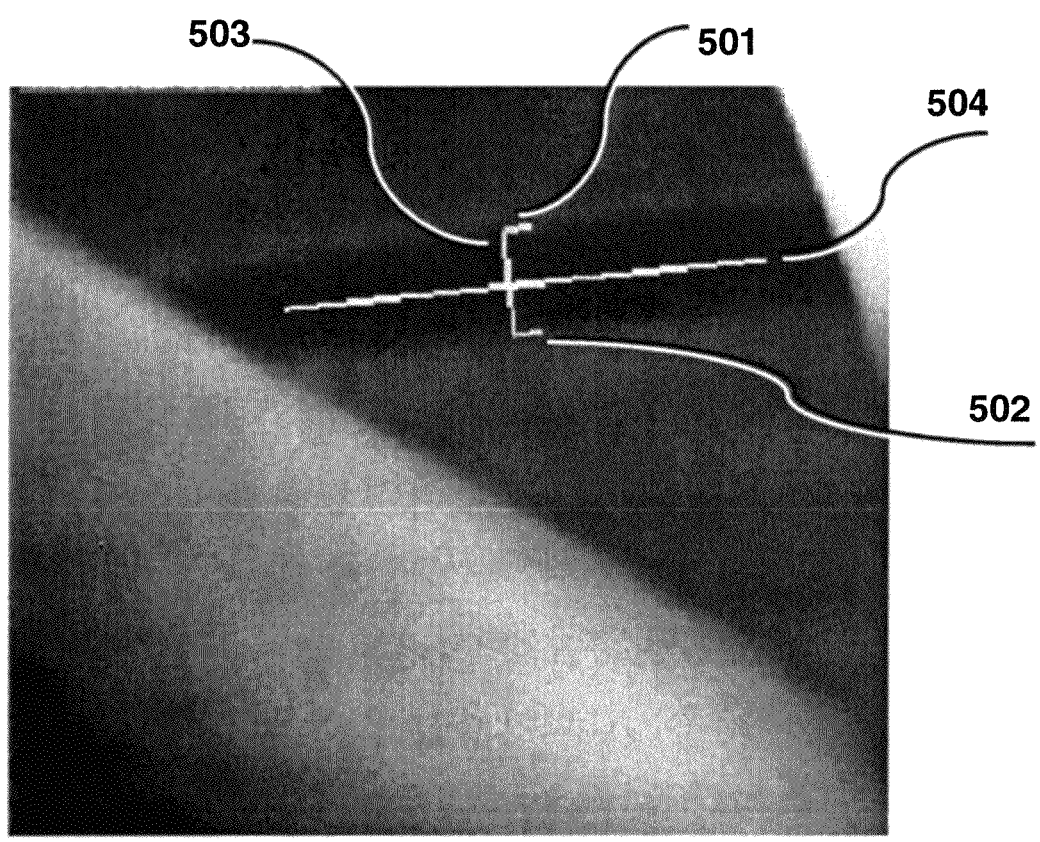
FIG. 5 illustrates a gap width measurement in accordance with an aspect of the present invention.

FIG. 5 shows one sample infra-red image where the gap is measured. The image shows calculated lines 501 and 502, corresponding to extracted edges and touching or crossing line 503 which may be perpendicular to at least 501 or 502. The main axis 504 of the gap is also shown, which may be used to facilitate gap measurement. A line 503 may also be predefined, for instance by a user. The size of the gap is determined by the length of 503 between 501 and 502. One may also determine at least one point that has to be on a line 503 and line 503 in such a case has to be perpendicular to at least 501 or 502 or 504.

The method as provided herein with various aspects of the present invention has been tested extensively on Row2 and Row3 blades over several hours each on a Siemens turbine. Image sequences were captured at real-time (30 frames per second). It has been demonstrated that one can automatically and accurately measure the gap between rows of blades for long periods of time for instance over 6 hours or even longer. The gap can be measured with a high accuracy, for instance with an accuracy of 0.1 mm.

The blades between which the gap distance is being measured are part of a rotating rotor. In one embodiment of the present invention the IR camera is triggered by a once per revolution (OPR) sensor and a processor. The processor triggers the camera at a specific moment so that the gap can be viewed at pre-defined phases or offsets relative to an OPR trigger. In one embodiment of the present invention the camera is triggered by an external trigger enabling to record images of the blade gap at a high rotation speed of the turbine.

In one embodiment of the present invention the rotating blades are rotating in a turbine running in a hot mode with the blades rotating with a rotational speed of greater than 300 rotations or revolutions per minute in an environment or atmosphere with a temperature greater than 300 degrees Fahrenheit. In one embodiment of the present invention a processor triggers the IR camera to take at least one image of the blades per second and the processor calculates the gap between the blades at least one every second.

The measured gap between blades can be applied as an indicator of the performance of a turbine. In one embodiment of the present invention one applies a certain range for the gap as an indicator of at least adequate performance of the turbine. If the gap exceeds this range an alarm may be triggered by the processor. In one embodiment of the present invention a change in gap size is used as a performance indicator. In one embodiment of the present invention a lack of significant change in the size of a gap may be applied as an indication of a steady-state operation of the turbine.

The methods as provided herein are, in one embodiment of the present invention, implemented on a system or a computer device. A system illustrated in FIG. 6 and as provided herein is enabled for receiving, processing and generating data. The system is provided with data that can be stored on a memory 1701. Data may be obtained from a sensor such as a camera for instance an IR high-speed camera or from any other data relevant source. Data may be provided on an input 1706. Such data may be image data or any other data that is helpful in a system as provided herein. The processor is also provided or programmed with an instruction set or program executing the methods of the present invention that is stored on a memory 1702 and is provided to the processor 1703, which executes the instructions of 1702 to process the data from 1701. Data, such as image data or any other data triggered or caused by the processor can be outputted on an output device 1704, which may be a display to display images or a data storage device. The processor also has a communication channel 1707 to receive external data from a communication device and to transmit data to an external device. The system in one embodiment of the present invention has an input device 1705, which may include a keyboard, a mouse, a pointing device, one or more cameras or any other device that can generate data to be provided to processor 1703.

Figure 6:
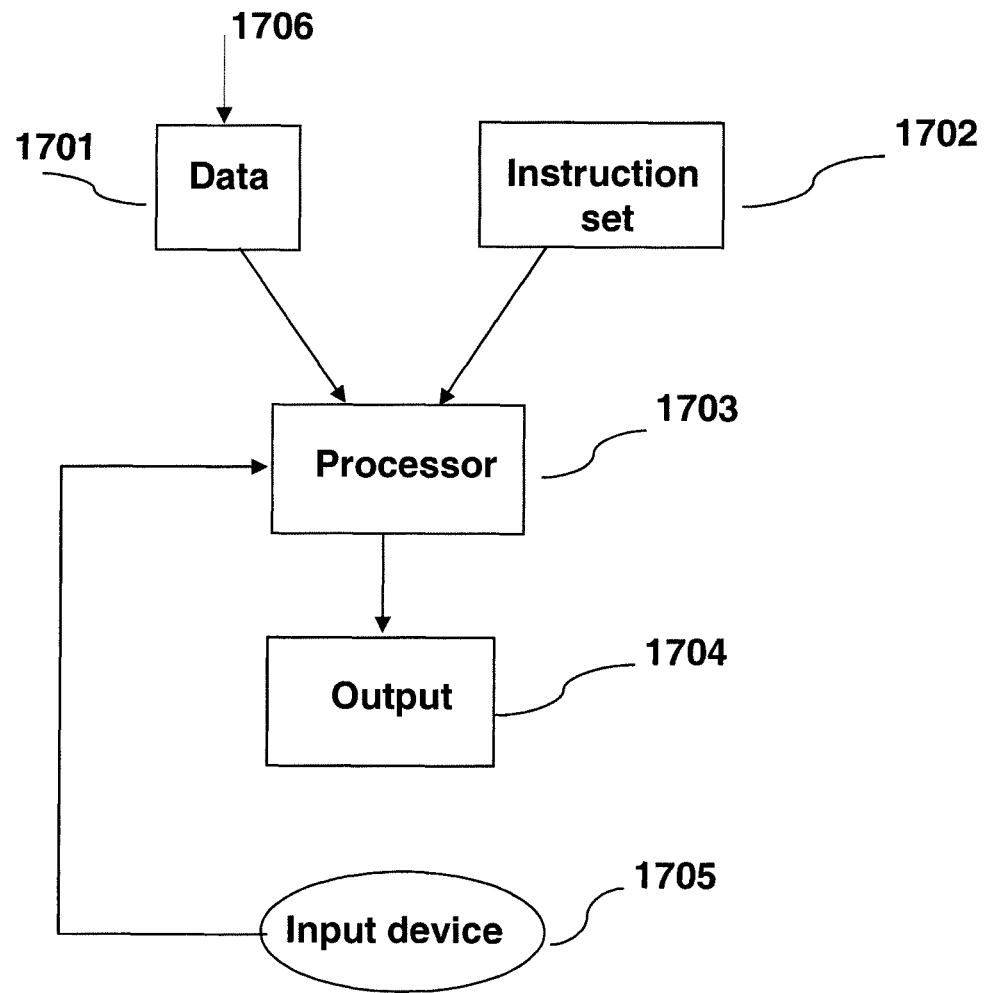
FIG. 6 illustrates a processor based system in accordance with an aspect of the present invention.

The processor can be dedicated or application specific hardware or circuitry. However, the processor can also be a general CPU, a controller or any other computing device that can execute the instructions of 1702. Accordingly, the system as illustrated in FIG. 6 provides a system for processing data resulting from a camera or any other data source and is enabled to execute the steps of the methods as provided herein as one or more aspects of the present invention.

In accordance with one or more aspects of the present invention methods and systems for automatically monitoring and measuring a gap in a moving part of a machine such as a turbine from image data generated by a camera have been provided.

Thus, novel systems and methods and steps implementing the methods have been described and provided herein.

It is to be understood that the present invention may be implemented in various forms of hardware, software, firmware, special purpose processors, or a combination thereof.

In one embodiment, the present invention may be implemented in software as an application program tangibly embodied on a program storage device. The application program may be uploaded to, and executed by, a machine comprising any suitable architecture.

It is to be understood that, because some of the constituent system components and method steps depicted in the accompanying figures may be implemented in software, the actual connections between the system components (or the process steps) may differ depending upon the manner in which the present invention is programmed. Given the teachings of the present invention provided herein, one of ordinary skill in the related art will be able to contemplate these and similar implementations or configurations of the present invention.

While there have been shown, described and pointed out fundamental novel features of the invention as applied to preferred embodiments thereof, it will be understood that various omissions and substitutions and changes in the form and details of the methods and systems illustrated and in its operation may be made by those skilled in the art without departing from the spirit of the invention. It is the intention, therefore, to be limited only as indicated by the scope of the claims.

The invention claimed is:

1. A method to measure a width of a gap between two moving parts in a machine, comprising:
   recording an image of the gap with an infra-red camera and storing the image as image data, wherein the gap is between two adjacent blades in a rotating turbine rotor of a gas turbine;
   a processor extracting a first and a second edge related to the gap from the image data;
   the processor applying a Hough transform to a plurality of pixels of the first edge to determine a first line and to a plurality of pixels of the second edge to determine a second line, substantially parallel to the first line and applying voting related to the plurality of pixels of the first edge to select line parameters of pixels in a majority;
   the processor applying a line through at least one pre-defined point that crosses the first and second lines;
   the processor determining the width of the gap from a length of the line through the at least one pre-defined point that crosses the first and second lines; and
   determining a performance of the gas turbine based on the width of the gap.

2. The method of claim 1, wherein the Hough transform applies voting related to the plurality of pixels of the first edge to eliminate line parameters caused by noise in the image data.

3. The method of claim 1, wherein a position of the line through at least one pre-defined point that crosses the first and second lines is determined by a user.

4. The method of claim 1, wherein the width of the gap is determined a plurality of times over a period of at least 6 hours.

5. The method of claim 1, wherein the width of the gap is measured with an accuracy of at least 0.1 mm.

6. The method of claim 1, wherein the first and second edges related to the gap are extracted from the image data by a Canny edge detector.

7. The method of claim 1, wherein the moving parts are rotating parts with a rotational speed of more than 300 revolutions per minute.

8. The method of claim 1, wherein the two adjacent blades are rotating with a rotational speed of at least 300 revolutions per minute in an atmosphere with a temperature of at least 300° F.

9. The method of claim 1, wherein a range of gap widths is used as an indicator of at least adequate performance of the gas turbine.

10. The method of claim 1, wherein the width of the gap indicates steady-state operation of the gas turbine.

11. A system to measure a width of a gap between two moving parts in a machine, comprising:
   an infra-red camera to record an image of the gap, wherein the gap is between two adjacent blades in a rotating turbine rotor of a gas turbine;
   a memory to store the image of the gap as image data;
   a processor to execute instructions to perform the steps:

extracting a first and a second edge related to the gap from the image data;

applying a Hough transform to a plurality of pixels of the first edge to determine a first line and to a plurality of pixels of the second edge to determine a second line and applying voting related to the plurality of pixels of the first edge to select line parameters of pixels in a majority;

applying a line through at least one pre-defined point that crosses the first and second lines;

determining the width of the gap from a length of the line through the at least one pre-defined point that crosses the first and second lines; and determining a performance of the gas turbine based on the width of the gap.

12. The system of claim 11, wherein the Hough transform applies voting related to the plurality of pixels of the first edge to eliminate line parameters caused by noise in the image data.

13. The system of claim 11, wherein a position of the line through at least one pre-defined point that crosses the first and second lines is determined by a user.

14. The system of claim 11, wherein the width of the gap is determined a plurality of times over a period of at least 6 hours.

15. The system of claim 11, wherein the width of the gap is measured with an accuracy of at least 0.1 mm.

16. The system of claim 11, wherein the first and second edges related to the gap are extracted from the image data by a Canny edge detector.

17. The system of claim 11, wherein the moving parts are rotating parts with a rotational speed of more than 300 revolutions per minute.

18. The system of claim 11, wherein the two adjacent blades are rotating with a rotational speed of at least 300 revolutions per minute in an atmosphere with a temperature of at least 300° F.

19. The system of claim 11, wherein a range of gap widths is used as an indicator of at least adequate performance of the gas turbine.

20. The system of claim 11, wherein a width outside the range of gap widths triggers an alarm.

* * * * *